United States Patent [19]

Patel et al.

[11] 4,207,900

[45] Jun. 17, 1980

[54] INSERT MOLDED CATHETER AND METHOD

[75] Inventors: Bhupendra C. Patel, Elgin; Russell J. Schweizer, Crystal Lake, both of Ill.; Jesse C. Smith, St. Petersburg Beach, Fla.

[73] Assignee: The Kendall Company, Boston, Mass.

[21] Appl. No.: 921,696

[22] Filed: Jul. 3, 1978

[51] Int. Cl.² ............................................. A61M 25/00
[52] U.S. Cl. ............................................... 128/349 B
[58] Field of Search ........................... 128/348–351, 128/246, 325, 344

[56] References Cited

U.S. PATENT DOCUMENTS

| | | | |
|---|---|---|---|
| 3,385,301 | 5/1968 | Harautuneian | 128/349 BV |
| 3,547,126 | 12/1970 | Birtwell | 128/349 B |
| 3,805,794 | 4/1974 | Schlesinger | 128/349 R |
| 3,811,450 | 5/1974 | Lord | 128/349 B |
| 3,989,571 | 11/1976 | Harautuneian | 128/349 B |

Primary Examiner—Dalton L. Truluck
Attorney, Agent, or Firm—Powell L. Sprunger

[57] ABSTRACT

A catheter comprising, an elongated shaft having a main lumen extending through the shaft, and an inflation lumen extending through a wall of the shaft. The catheter has a tip molded directly onto a distal end of the shaft, and a connecter molded directly onto a proximal end of the shaft.

3 Claims, 6 Drawing Figures

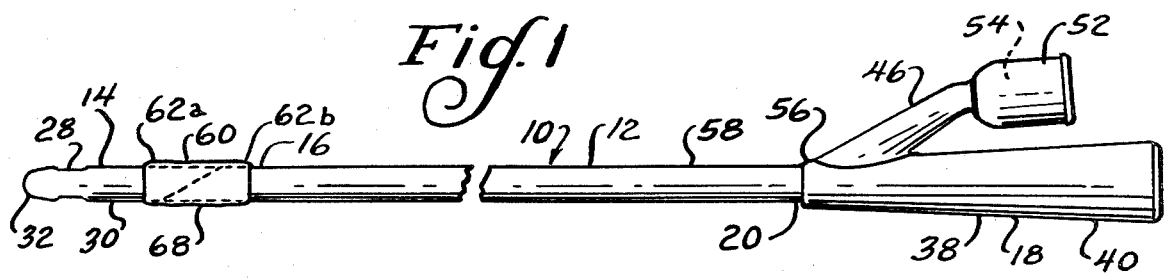
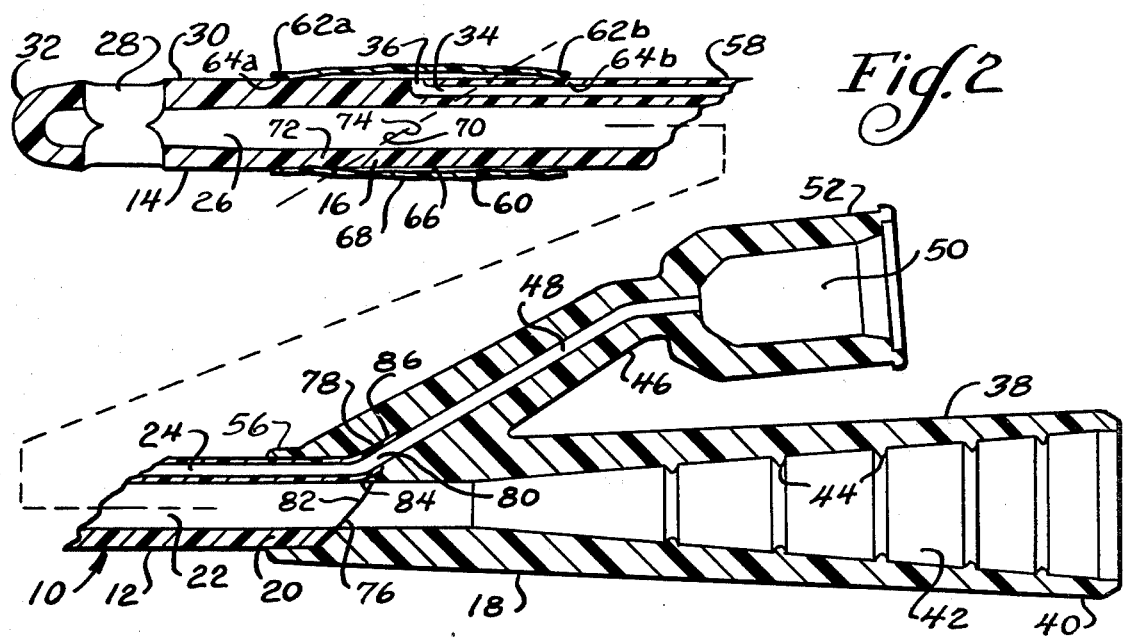
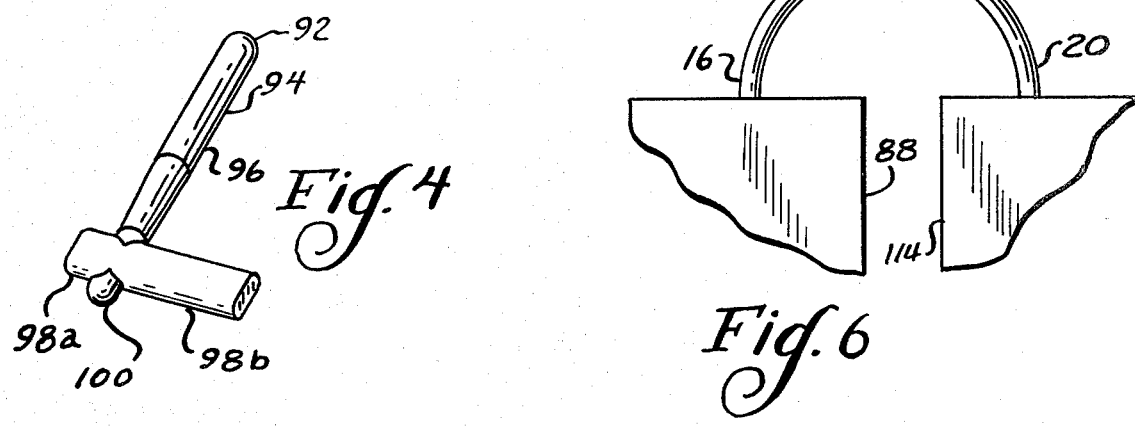
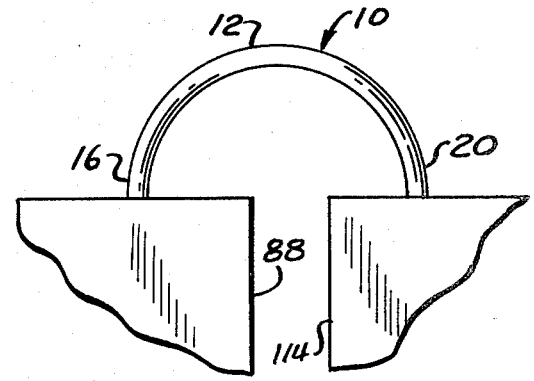

INSERT MOLDED CATHETER AND METHOD

BACKGROUND OF THE INVENTION

The present invention relates to catheters.

A various assortment of catheters, such as urinary catheters and endotracheal tubes, have been proposed for use in patients. In the case of urinary catheters, Foley catheters are commonly constructed with a shaft having a drainage lumen and an inflatable balloon adjacent a distal end of the shaft. During placement, a distal end of the catheter is passed through the patient's urethra until the balloon and drainage eyes, which communicate with the drainage lumen, are located in the patient's bladder, and the balloon is inflated through an inflation lumen to retain the catheter in place. During catheterization, urine drains through the drainage eyes and lumen and through a drainage tube connected to a proximal end of the catheter to a drainage bag for collection therein.

Conventional catheters of this sort were made from latex rubber through dipping techniques known to the art. In time, it was discovered that the latex catheters were not completely satisfactory since layers of the dipped material occasionally became delaminated during use, thus causing blockage in the inflation lumen and obstructing deflation of the balloon when it was necessary to remove the catheter from the patient. As a result, it became desirable to construct the catheter shaft from a material which may be extruded in order to prevent possible blockage of the inflation lumen, and reduce the cost of the catheter to the patient due to simplified manufacturing techniques.

In turn, the materials which appeared satisfactory for use as a shaft posed new problems in construction of the catheter. For example, it became necessary to find suitable materials for the balloon which are sufficiently elastic to permit inflation during use, and which are compatible with the selected shaft for bonding purposes. Frequently, materials which appeared otherwise satisfactory for the catheter shaft and balloon proved to be incompatible when attempts were made to bond the balloon to the shaft through use of adhesive or sealing. In addition, it became necessary to secure a tip to the distal end of the extruded shaft, and a connector to the proximal end of the shaft. Such tips and connecters have been formed separately, and have been adhered to the shaft. However, in the case of the connecters, it is necessary to establish communication between lumens in the connecter and the associated inflation and drainage lumens in the shaft. In the case of the tips, it is necessary to obtain a sufficient bond of the tip to the distal end of the shaft while closing the distal end of the inflation lumen. In both cases, difficulties have been encountered in obtaining the proper alignment of lumens and achieving the desired bond. In addition, it has been necessary in the past to separately form an opening in the outer surface of the shaft to obtain communication between the inflation lumen and a cavity beneath the balloon. All of the excessive operations and difficulties associated with construction of the catheter deleteriously affect the capability of providing the catheter, which is considered a disposable item, at a significantly reduced cost.

SUMMARY OF THE INVENTION

A principal feature of the present invention is the provision of a catheter of simplified construction and reduced cost.

The catheter of the present invention comprises, an elongated shaft having a main lumen extending through the shaft, and an inflation lumen extending through a wall of the shaft. The catheter has a tip molded directly onto a distal end of the shaft, with the tip having a lumen communicating with the main lumen of the shaft, and at least one opening adjacent a distal end of the tip communicating with the tip lumen. The molded tip defines a distal end portion of the inflation lumen and an aperture at an outer surface of the tip. The distal end of the shaft and the proximal end of the tip have complementary beveled portions defining juncture surfaces which are bonded together. The catheter has a connecter directly bonded onto a proximal end of the shaft, with the connector having a lumen communicating with the shaft drainage lumen, and an inflation lumen in a side arm communicating with the inflation lumen of the shaft. The connecter and proximal end of the shaft have complementary beveled portions defining juncture surfaces, and the shaft has a proximal end portion defined by the bevel which is outwardly flared in the molded connecter. The catheter also has a sleeve of elastic material secured to the catheter in spaced circumferential zones and defining a cavity communicating with the inflation lumen.

A feature of the present invention is that the beveled portions at the proximal and distal ends of the catheter shaft define an enlarged surface area to achieve an enhanced bond between the shaft and the catheter tip and connecter.

Another feature of the invention is that the distal end portion of the inflation lumen is automatically formed in the tip during molding of the tip.

A further feature of the invention is that an aperture is defined at the distal end of the inflation lumen in the tip during molding of the tip.

Yet another feature of the invention is that the outwardly flared proximal end portion of the catheter shaft ensures structural continuity and integrity between the inflation lumens of the shaft and connecter.

A feature of the present invention is that the catheter shaft is insert molded onto the tip and connecter in a simplified manner without the use of adhesive.

A further feature of the invention is that the catheter may be made at a reduced cost.

Another feature of the invention is the provision of methods for constructing the catheter of the present invention.

Further features will become more fully apparent in the following description of the embodiments of this invention and from the appended claims.

DESCRIPTION OF THE DRAWINGS

In the drawings:

FIG. 1 is a fragmentary elevational view of a catheter of the present invention;

FIG. 2 is a fragmentary sectional view of the catheter of FIG. 1;

FIG. 4 is a perspective view of a main pin for use in the mold of FIG. 3;

FIG. 6 is a fragmentary schematic view of separate molds being used to simultaneously form a tip and connecter onto a catheter shaft.

DESCRIPTION OF THE PREFERRED EMBODIMENTS

Figure 3:
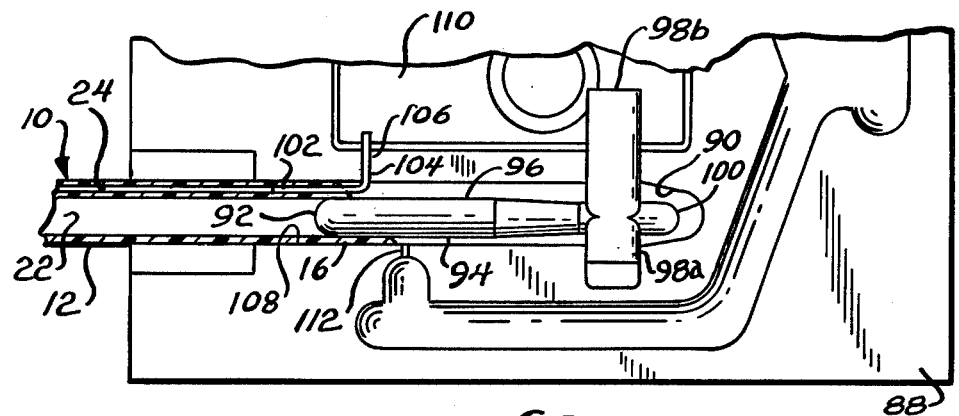
FIG. 3 is a fragmentary plan view of a mold for forming a tip on a distal end of a catheter shaft.
Figure 5:
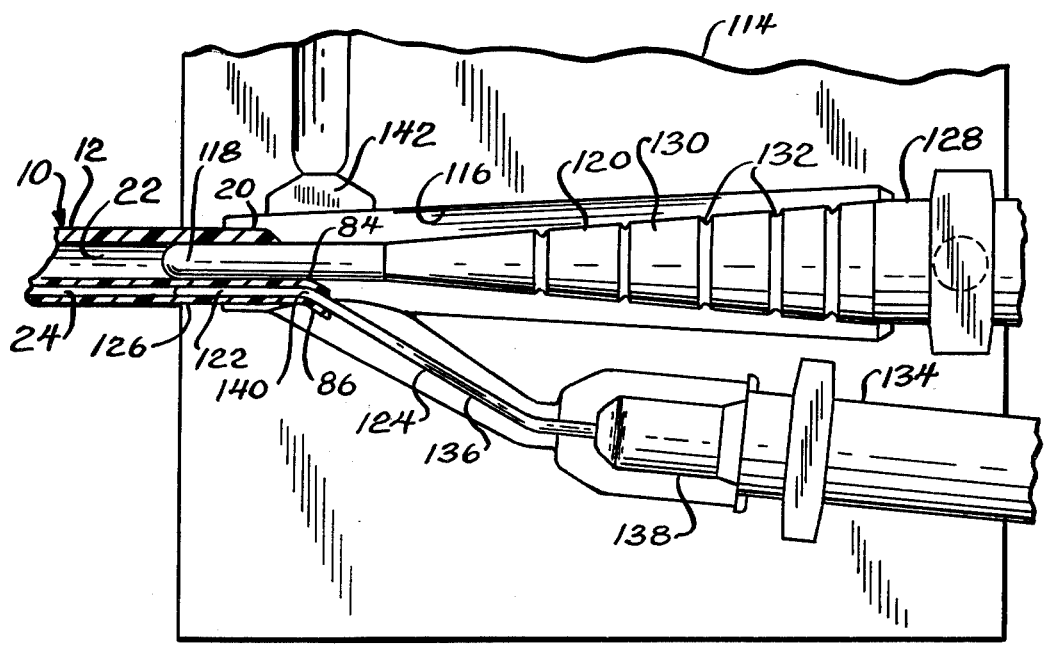
FIG. 5 is a fragmentary plan view of a mold for forming a connecter onto a proximal end of a catheter shaft.

Referring now to FIGS. 1 and 2, there is shown a catheter generally designated 10 having an elongated extruded shaft 12, a tip 14 secured to a distal end 16 of the shaft 12, and a connecter 18 secured to a proximal end 20 of the shaft 12. The shaft 12 has a main or drainage lumen 22 extending through the shaft, and an inflation lumen 24 extending through a wall of the shaft.

The tip 14 has a main lumen 26 communicating with the main lumen 22 of the shaft 12, and a pair of drainage eyes or openings 28 extending to an outer surface 30 of the tip 14, and communicating with the main lumen 26 of the tip. The tip has a closed distal end 32, and the tip defines a distal end portion 34 of the inflation lumen 24 and an aperture 36 at the outer surface 30 of the tip communicating with the lumen portion 34.

The connecter 18 has a connecting portion 38 defining a proximal end 40 of the catheter 10 and defining a main lumen 42 of the connecter 18 communicating with the drainage lumen 22 of the shaft 12. As shown, the proximal end of the connecter lumen 42 is enlarged to receive an adapter of a drainage tube (not shown), and the connecter 18 has a plurality of annular sealing rings 44 in the lumen 42 to snugly engage against the drainage tube adapter. The connecter 18 has a side arm 46 defining an inflation lumen 48 which communicates with the inflation lumen 24 of the shaft 12, and a recess 50 at a proximal end 52 of the side arm 46 to receive suitable valve means 54 for controlling passage of fluid through the inflation lumen of the shaft and connecter. As shown, the connecter 18 has a distal annular flange 56 engaging against an outer surface 58 of the shaft 12 and enclosing the proximal end 20 of the shaft.

The catheter also has an annular sleeve 60 of elastic material forming a balloon adjacent a distal end of the catheter. The sleeve 60 has a pair of opposed ends 62a and 62b which are respectively secured in circumferential zones 64a and 64b to the outer surface 30 of the tip 14 and the outer surface 58 of the shaft 12. In this configuration, the sleeve 60 defines a cavity 66 underlying a central portion 68 of the sleeve 60 which communicates with the inflation lumen through the tip aperture 36.

As shown in FIG. 2, the shaft 12 has a beveled distal end which defines a tapered juncture surface 70 disposed at an acute angle relative to the lower surface of the shaft as shown in the drawing. In turn, the tip 14 has a beveled proximal end 72 which defines a complementary juncture surface 74 disposed at an obtuse angle relative to the lower surface of the shaft as presented in the drawing, with the surfaces 70 and 74 facing each other and being secured together to bond the tip 14 to the shaft 12. As shown, the tip aperture 36 is located intermediate ends of the beveled portions of the tip and shaft.

The shaft 12 also has a beveled proximal end defining a juncture surface 76 disposed at an acute angle relative to an upper surface of the shaft as presented in the drawings, such that the proximal beveled shaft portion defines a tapered end portion 78 containing the proximal end 80 of the shaft inflation lumen 24, with the inflation lumen end 80 being disposed at the apex of the acute angle. The connecter has a complementary beveled juncture surface 82 which is disposed at an obtuse angle relative to the upper surface of the shaft as presented in the drawing. In a preferred form, the acute angles at both the proximal and distal ends of the shaft may range from 30 to 45 degrees. The juncture surfaces 76 and 82 of the shaft 12 and connecter 18 face each other and are secured together inside the connecter 18. As shown, the shaft 12 may be longitudinally severed along a line 84 at the proximal end 20 of the shaft 12, with the line 84 being located intermediate the inflation lumen 24 and the opposed surface of the catheter shaft, such that the severance line 84 defines a flap 86 at the tapered end portion 78 containing the proximal end 80 of the shaft inflation lumen 24. As shown, the flap 86 is outwardly flared in the connecter 18, such that the flap 86 defines a curve in the proximal end 80 of the shaft drainage lumen 24, and spaces the proximal end 80 of the inflation lumen 24 from the main lumens 22 and 42 of the shaft 12 and connecter 18, respectively. In this manner, the outwardly flared flap 86 assures continuity and integrity between the inflation lumen 24 of the shaft 12 and the inflation lumen 48 of the connecter 18 without leakage into the main lumens of the catheter shaft or connecter. However, it is noted that the tapered end portion 78 of the shaft 12 may be placed in the outwardly flared configuration without the severance line 84 due to the tapered configuration of the shaft proximal end 20.

As will be seen below, the tip 14 and connecter 18 are molded directly onto the distal and proximal ends of the shaft, such that the tip and connecter are bonded to the shaft without the use of adhesive. In a preferred form, the shaft 12 and sleeve 60 may be extruded from a suitable elastic material. The tip 14 and connecter 18 may then be molded onto the catheter shaft 12, and the sleeve 60 may be bonded onto the tip and shaft after removal of the catheter from the molds. In a preferred form, the shaft 12 and sleeve 60 may be extruded from the same material of which the tip 12 and connecter 18 are molded, and, in a suitable form, the shaft 12, tip 14, connecter 18, and sleeve 60 may be constructed from a thermoplastic elastomer such as Kraton, a trademark of Shell Oil Company.

Referring now to FIG. 3, there is shown a mold 88 having a cavity 90 for insert molding the distal end 16 of the catheter shaft 12 onto a tip as will be described below. First, the distal end 16 of the catheter shaft 12 is severed at an angle to define the tapered end portion of the catheter shaft. Next, a proximal end 92 of a main pin 94 is inserted into the distal end of the shaft main lumen 22 in order to close the distal end of the main lumen 22. With reference to FIGS. 3 and 4, the main pin 94 has an elongated core 96, and a pair of opposed ears 98a and 98b extending outwardly from the core 96 adjacent a distal end 100 of the main pin 94.

As shown in FIG. 3, a proximal end 102 of an auxiliary pin 104 is inserted into the distal end of the shaft inflation lumen 24 in order to close the distal end of the inflation lumen. As shown, the auxiliary pin 104 has a central portion 105 extending distally from the shaft and aligned with the inflation lumen 24. The pin 104 also has an outwardly turned distal end portion 106 which is spaced from the distal end of the shaft 12, and which is located intermediate the ends of the beveled distal shaft portion.

necter. Of course, the cavities for the tip and connecter may be placed in a single mold for simultaneous molding of the tip and connecter to the catheter shaft in one mold, if desired.

The foregoing detailed description is given for clearness of understanding only, and no unnecessary limitations should be understood therefrom, as modifications will be obvious to those skilled in the art.

We claim:

1. A catheter, comprising:
   an elongated shaft having a main lumen extending through the shaft, and an inflation lumen extending through a wall of the shaft, said shaft having a beveled distal end defining a first juncture surface disposed at an acute angle relative to an outer surface portion of the shaft;
   a tip directly molded onto said first shaft juncture surface with said tip having a complementary beveled proximal end defining a first juncture surface bonded to the shaft juncture surface and being disposed at an obtuse angle relative to said outer shaft surface portion, said tip having a lumen communicating with said main lumen of the shaft and at least one opening adjacent a distal end of the tip communicating with the tip lumen, said proximal beveled portion of the tip defines a distal end portion of the inflation lumen and an aperture at an outer surface of the tip communicating with the inflation lumen;
   a sleeve of elastic material secured to the catheter in spaced circumferential zones and defining a cavity communicating with said inflation lumen;
   said shaft having a beveled proximal end defining a second juncture surface disposed at an acute angle relative to an outer surface portion of the shaft adjacent the inflation lumen at a proximal end of the shaft, and defining a tapered end portion adjacent the juncture of said outer surface portion and said second juncture surface; and
   a connecter directly molded onto said second shaft juncture surface with said connecter having a complementary beveled juncture surface bonded to said second shaft juncture surface, said connecter having a lumen communicating with the main shaft lumen, and a side arm defining an inflation lumen communicating with a proximal end of the inflation lumen, with said tapered shaft portion being outwardly flared and defining a curved proximal end portion of the shaft inflation lumen and joining the inflation lumens of the shaft and connecter.

2. The catheter of claim 1 wherein said shaft is longitudinally severed outside the inflation lumen at a proximal end of the shaft intermediate the inflation lumen and an opposed outer surface of the shaft, with the severance line defining a flap containing the proximal end of said inflation lumen; said shaft flap being outwardly flared in the connecter and defining a curve in the proximal end of the shaft inflation lumen connecting the shaft and connecter inflation lumens.

3. A catheter, comprising:
   an elongated shaft having a main lumen extending through the shaft, and an inflation lumen extending through a wall of the shaft, said shaft being longitudinally severed along a line at the proximal end of the shaft intermediate the inflation lumen and an opposed outer surface of the shaft, with the severance line defining a flap containing the proximal end of said inflation lumen, said shaft also having a leveled distal end defining a first juncture disposed at an acute angle relative to an outer surface portion of the shaft, said shaft having a leveled proximal end defining a second juncture surface disposed at an acute angle relative to an outer surface portion of the shaft adjacent the inflation lumen at a proximal end of the shaft, and defining a tapered end portion adjacent the juncture of said outer surface portion and said second juncture surface; and
   a connecter directly molded onto said second shaft juncture surface with said connecter having a complementary leveled juncture surface bonded to said second shaft juncture surface, said connecter having a lumen communicating with the main shaft lumen, and a side arm defining an inflation lumen communicating with a proximal end of the inflation lumen, with said tapered shaft portion being outwardly flared and defining a curved proximal end portion of the shaft inflation lumen and joining the inflation lumens of the shaft and connecter.

* * * * *